(12) United States Patent
Hasse

(10) Patent No.: US 7,902,342 B2
(45) Date of Patent: Mar. 8, 2011

(54) METHOD FOR PRODUCING GASEOUS DIAZOALKANES

(75) Inventor: Jürgen Hasse, Waltrop (DE)

(73) Assignee: Dynamit Nobel GmbH Explosivstoff-und Systemtechnik, Leverkusen (DE)

( * ) Notice: Subject to any disclaimer, the term of this patent is extended or adjusted under 35 U.S.C. 154(b) by 0 days.

(21) Appl. No.: 11/629,149

(22) PCT Filed: Jun. 23, 2005

(86) PCT No.: PCT/EP2005/006808
§ 371 (c)(1),
(2), (4) Date: Jan. 30, 2007

(87) PCT Pub. No.: WO2006/000414
PCT Pub. Date: Jan. 5, 2006

(65) Prior Publication Data
US 2007/0249817 A1    Oct. 25, 2007

(30) Foreign Application Priority Data
Jun. 23, 2004  (DE) .......................... 10 2004 030 371

(51) Int. Cl.
*C07C 245/16* (2006.01)
(52) U.S. Cl. ........................ 534/558; 534/565
(58) Field of Classification Search .................... 534/565
See application file for complete search history.

(56) References Cited

U.S. PATENT DOCUMENTS

| 3,681,362 | A | * | 8/1972 | Nagata et al. | 540/579 |
| 3,963,698 | A | * | 6/1976 | Hecht et al. | 536/27.81 |
| 5,817,778 | A |   | 10/1998 | Archibald et al. | |
| 5,854,405 | A | * | 12/1998 | Archibald et al. | 534/565 |
| 6,962,983 | B2 | * | 11/2005 | Warr et al. | 534/565 |
| 7,300,921 | B2 | * | 11/2007 | McAlpine et al. | 514/25 |
| 2002/0188112 | A1 |  | 12/2002 | Warr et al. | |

OTHER PUBLICATIONS

Adamson et al., Chemical Abstracts, 29:5413d-e, 1935.*
Adamson et al., "Preparation of Diazomethane and its Homologues in the Free State", Nature, 135(3420), 833, May 18, 1935.*
Hawley's Condensed Chemical Dictionary, 14th Edition, John Wiley & Sons, 2002, "diazomethane".*
Adamson et al., "Improved Preparations of Aliphatic Diazo-Compounds, and Certain of Their Properties", Journal of the Chemical Society, 1551-1556, 1937.*
Proctor et al., "Development of a Continuous Process for the Industrial Generation of Diazomethane", Organic Process Research and Development, 6, 884-892, 2002.*
Adamson et al. 1937, Improved Preparations of Aliphatic Diazo-Compounds, and Certain of Their Properties, Journal of the Chemical Society. (1937).

* cited by examiner

*Primary Examiner* — Fiona T Powers
(74) *Attorney, Agent, or Firm* — Fulbright & Jaworski L.L.P.

(57) ABSTRACT

The invention relates to a method for producing diazoalkanes, which is characterized by dissolving a diazoalkane precursor in a first solvent, dissolving a base in a second solvent, allowing the substances to react in a reactor while forming the diazoalkane and removing the diazoxaline under reduced pressure. The inventive method is especially suitable for producing diazomethane.

25 Claims, No Drawings

METHOD FOR PRODUCING GASEOUS DIAZOALKANES

This is a §371 of PCT/EP2005/006808 filed Jun. 23, 2005, which claims priority from German Patent Application No. 10 2004 030 371.1 filed Jun. 23, 2004.

The invention relates generally to a process for preparing gaseous diazoalkanes and especially to a process for preparing diazomethane.

Diazoalkanes play a major role as intermediate products or reactants in organic synthesis, particularly during etherification reactions of NH bonds, OH bonds or acid bonds, during syntheses of heterocyclic compounds, during additions to double-bond systems or during insertion reactions under mild conditions.

A process for preparing diazomethane that is described in WO 01/47869 includes the following steps:
addition of a diazomethane precursor dissolved in a first solvent and
addition of a base dissolved in a second solvent (preferably water)
into a reaction vessel in which these substances react, forming diazomethane. The diazomethane obtained is removed with the aid of a diluent gas, this stream of gas being substantially free from solvents and solvent vapours.

Disadvantages of this process are that
By virtue of the intense stream of inert gas that is necessary for reasons of safety, considerable quantities of water (the preferred second solvent with this process) are stripped out of the reaction vessel, which have to be withdrawn from the stream of gas via large-area condensers and/or dryers if they interfere with conversion reactions. As a result, high investment costs are incurred in connection with plant construction.

For reasons of safety, the diazomethane content in the gas stream has to be kept below about 15%. This requires an elaborate and therefore expensive online measurement (e.g. by means of infrared spectroscopy) with associated inert-gas control technology.

Diazoalkanes are highly toxic and carcinogenic. In the case where use is made of a diluent inert gas in the preparation of diazoalkanes, working necessarily has to proceed with slight excess pressure. In the event of leaks in the plant, diazoalkane gases therefore immediately escape into the ambient air and may endanger people there.

The object of the invention is to overcome the disadvantages of the state of the art and to provide a process for preparing gaseous diazoalkanes, and in particular for preparing diazomethane, that manages without the aid of a diluent gas.

The object is achieved by a process for preparing gaseous diazoalkanes wherein a diazoalkane precursor is dissolved in a first solvent, and a base is dissolved in a second solvent, the substances react in a reaction vessel, forming the diazoalkane, and the diazoalkane obtained is removed under reduced pressure compared to normal pressure.

Surprisingly, it has been found that, within a pressure range lying below normal pressure, diazomethane exhibits explosion limits similar to those in the case of dilution with inert gas, and cannot be caused to explode by ignition sparks.

The following compounds may be employed, for example, as diazoalkane precursor: N-alkyl-N-nitroso compounds such as N-alkyl-N-nitrosocarboxamides (e.g. N-alkyl-N-nitrosourea), N-alkyl-N-nitrosourethanes, N-alkyl-N-nitrosoarylsulfonamides (e.g. N-alkyl-N-nitrosotoluene-sulfonamides) or N-alkyl-N-nitrosoaminoketones.

Diazomethane may be prepared as the preferred diazoalkane with the process according to the invention. By way of diazomethane precursor, all compounds that are known for this purpose and that are described, for example, in WO 01/47869 may be employed, in particular N-methyl-N-nitroso compounds such as N-methyl-N-nitrosocarbonamides (e.g. N-methyl-N-nitrosourea), N-methyl-N-nitrosourethanes, N-methyl-N-nitrosoarylsulfonamides (e.g. N-methyl-N-nitrosotoluenesulfonamide) or N-methyl-N-nitrosoaminoketones.

Inorganic bases such as, for example, lithium hydroxide, sodium hydroxide, potassium hydroxide, rubidium hydroxide, caesium hydroxide and barium hydroxide may be employed as the base. Organic bases such as, for example, N-heterocyclic compounds may likewise be employed as the base. For reasons of cost, the alkali hydroxides sodium hydroxide or potassium hydroxide are preferably employed.

The first and second solvents may be the same or different.

By way of first solvent, in which the diazoalkane precursor is dissolved, known solvents (e.g. known from WO 01/47869) are preferably employed that exhibit a high boiling point, a low vapour pressure and a high solubility in water. Furthermore, the first solvent is preferably not reactive with respect to diazoalkanes. By way of first solvent, arylalkyl ether, glycol ether, dimethyl formamide (DMF), dimethyl sulfoxide (DMSO) or ionic solvents, for example 1,3-dimethyliznidazolinium dimethyl phosphate, are employed in a particularly preferred manner. In a very particularly preferred manner, use is made of DMSO and/or di(ethylene glycol) ether. Mixtures of the stated solvents may also be employed.

The second solvent, in which the base is dissolved, may be selected from a solvent that can be employed as first solvent. In this connection the first and second solvents may be identical, but do not have to be. The second solvent is preferably water or preferably contains water.

The base (which may consist of several substances) is preferably employed in a quantity from 1 to 3 equivalents relative to the diazoalkane precursor. Particularly preferred is a quantity from 1.1 to 2 equivalents, so that the base is present in excess.

The diazoalkane precursor and the base may be added simultaneously or in succession and mixed together.

The term 'reduced pressure' is to be understood to mean a pressure range that is reduced in comparison with normal pressure. The reduced pressure range preferably amounts to 0 mbar to 800 mbar, particularly preferably 100 mbar to 300 mbar. The removal of the diazoalkane under reduced pressure may be carried out with the aid of an inert gas. However, the diazoalkane is preferably removed under reduced pressure without the aid of an inert gas.

The reaction is preferably carried out at temperatures from 10° C. to 80° C., particularly preferably from 20° C. to 50° C.

The reaction of diazoalkane generation may be carried out continuously or in batches.

The process according to the invention may be carried out in exemplary manner as follows (without a limitation of any kind being imposed by this description):

In a diazomethane-generation reactor an approximately 25% solution of N-methyl-N-nitrosotoluenesulfonamide in DMSO at 20° C. to 70° C. is mixed simultaneously or in succession with a 20% to 40% aqueous XOH solution. By means of an underpressure from 0 mbar to 800 mbar the dlazomethane that forms spontaneously is drawn into a conversion reactor or reaction scrubber, where it reacts to completion in the desired manner.

The process according to the invention has the advantage over processes known hitherto that the quantity of the inert gas can be reduced considerably, or the inert gas can be dispensed with entirely. At most, insignificant quantities of solvent vapour (such as, for example, water vapour) are stripped out of the diazoalkane generator, which, where appropriate, can be removed from the diazoalkane with small-area condensers or dryers. By virtue of the vacuum mode of operation, in the event of a leak occurring endangerment of the operating staff by the highly toxic and carcinogenic diazoalkane gases is ruled out. Moreover, the lowering of the diazoalkane concentration that is necessary for reasons of safety can be realised solely by an inexpensive pressure measurement. Safety investigations in respect of DAM in a vacuum have shown that at a partial pressure >150 mbar DAM can be caused to explode by means of an ignition spark. Therefore this 'concentration' of DAM should, as far as possible, not be exceeded in an industrial plant. If this partial pressure is supplemented with inert gas at normal pressure, this limit corresponds to a DAM concentration of about 15 vol. %—a value that is specified as the explosion limit at normal pressure for DAM.

In accordance with the invention the partial pressure of the diazoalkane arising—for example, of the diazomethane (DAM) arising—is measured continuously by means of infrared spectroscopy.

The following Examples are intended to elucidate the invention without limiting it:

EXAMPLES 1-3

In a 1.5 l double-walled glass reactor 531 g of aqueous 30% KOH solution are submitted and are heated, respectively, to 40° C., 55° C. and 70° C. By controlled dropwise addition of 405.8 g of 26.4% N-methyl-N-nitroso-p-toluenesulfonamide (MNTSA) solution in DMSO into this KOH solution, diazomethane (DAM) is generated and is aspirated in gaseous form into a glass reactor via a frit by means of vacuum at 500 mbar. The metered addition is effected in such a way that the diazomethane concentration in the gas phase does not exceed a partial pressure of 120 mbar. With a view to determining the DAM quantity and yield, this glass reactor is charged with an acid, for example with a solution of benzoic acid in DMF, so that the DAM aspirated via the frit reacts to completion immediately to form methyl benzoate, and the content thereof is determined analytically and can be utilized as an equivalent for DAM. The following table reproduces the results:

| Example No. | Reaction temperature [° C.] | DAM yield [%] |
|---|---|---|
| 1 | 40 | 32.8 |
| 2 | 55 | 28.4 |
| 3 | 70 | 23.3 |

Examples 4-6

The experimental set-up and the determination of the yield correspond to those of Experiments 1-3. 259.7 g of 25.9% N-methyl-N-nitroso-p-toluenesulfonamide solution in DMSO are added dropwise without interruption into the submitted 561 g of 30% KOH solution at 40° C. In the course of this procedure the vacuum is changed stepwise from 800 mbar via 500 mbar to 320 mbar by adapted feeding of a stream of argon. The metered addition of the nitrosomethyl component is effected in such a way that a DAM partial pressure of 150 mbar is not exceeded.

| Example No. | Reaction pressure [mbar] | DAM yield [%] |
|---|---|---|
| 4 | 800 | 41.0 |
| 5 | 500 | 46.4 |
| 6 | 320 | 47.6 |

Examples 7-9

The experimental arrangement corresponds to that of Experiments 1-3.

The 30% KOH solution is added in metered amounts into the reactor at 500 mbar in parallel with the 25.9% N-methyl-N-toluenesultonamide solution in DMSO at 40° C. while maintaining the DAM partial pressure of 150 mbar. In the experiments the ratio of KOH to the nitrosomethyl component is changed from 1.1 to 1.5.

| Example No. | Metering rate KOH solution [ml/min] | Metering rate MNTSA solution [ml/min] | Molar ratio KOH/MNTSA | DAM yield [%] |
|---|---|---|---|---|
| 7 | 0.330 | 1.466 | 1.1 | 47.2 |
| 8 | 0.375 | 1.466 | 1.25 | 47.6 |
| 9 | 0.450 | 1.466 | 1.5 | 60.9 |

Example 10

In a long-duration experiment over 4 hours the procedure is as in Experiments 7-9, in that a 22.5% MNTSA solution is added simultaneously in metered amounts to a 30% KOH solution.

| Example No. | Metering rate KOH solution [ml/min] | Metering rate MNTSA solution [ml/min] | Molar ratio KOH/MNTSA | DAM yield [%] |
|---|---|---|---|---|
| 10 | 0.450 | 1.735 | 1.5 | 68.3 |

Example 11

Deviating from Experiment 7, MNTSA in the ionic solvent 1,3-dimethylimidazolinium dimethyl phosphate (ECOENG 1111P produced by Solvent Innovation GmbH) in the form of an 8.0% solution was added in metered amounts in parallel with a 30% KOH solution.

| Example No. | Metering rate KOH solution [ml/min] | Metering rate MNTSA solution [ml/min] | Molar ratio KOH/MNTSA | DAM yield [%] |
|---|---|---|---|---|
| 11 | 0.450 | 4.381 | 1.5 | 11.3 |

The invention claimed is:
1. A process comprising dissolving a diazomethane precursor in a first solvent, dissolving a base in a second solvent, reacting the diazomethane precursor and the base in a reaction vessel to form gaseous diazomethane, and removing the gaseous diazomethane from the reaction vessel under reduced pressure.

2. A process according to claim 1, wherein the diazomethane precursor is a N-methyl-N-nitroso compound.

3. A process according to claim 2, wherein the first solvent comprises an aralkyl ether.

4. A process according claim 1, wherein the base is inorganic or organic.

5. A process according to claim 1, wherein the base is inorganic.

6. A process according to claim 1, wherein the base is organic.

7. A process according to claim 1, wherein the first solvent comprises at least one of an arylalkyl ether, a glycol ether, dimethyl formamide, dimethyl sulfoxide, or an ionic solvent.

8. A process according to claim 1, wherein the first solvent and second solvent are the same.

9. A process according to claim 2, wherein the second solvent comprises water.

10. A process according to claim 1, wherein the base is present in an amount of from 1 to 3 equivalents relative to the diazomethane precursor.

11. A process according to claim 1, wherein the diazomethane precursor and the base are added and mixed together simultaneously.

12. A process according to claim 1, wherein the diazomethane precursor and the base are added and mixed together in succession.

13. A process according to claim 1, wherein the gaseous diazomethane is removed at from 0 mbar to 800 mbar.

14. A process according to claim 13, wherein the gaseous diazomethane is removed at from 100 mbar to 300 mbar.

15. A process according to claim 1, wherein the reaction takes place at temperature of from 10° C. to 80° C.

16. A process according to claim 15, wherein the reaction takes place at a temperature of from 20° C. to 50° C.

17. A process according to claim 1, wherein the diazomethane precursor is N-methyl-N-nitrosocarbonamide, a N-methyl-N-nitrosourethane, a N-methyl-N-nitrosoarylsulfonamides or a N-methyl-N-nitrosoaminoketone.

18. A process according to claim 1, wherein the diazomethane precursor is an N-methyl-N-nitrosourea.

19. A process according to claim 1, wherein the diazomethane precursor is N-methyl-N-nitrosourea.

20. A process according to claim 1, wherein the diazomethane precursor is N-methyl-N-nitrosotoluenesulfonamide.

21. A process according to claim 3, wherein the diazomethane precursor is a N-methyl-N-nitrosocarbonamide, a N-methyl-N-nitrosourethane, a N-methyl-N-nitrosoarylsulfonamide or a N-methyl-N-nitrosoaminoketone.

22. A process according to claim 3, wherein the diazomethane precursor is N-methyl-N-nitrosotoluenesulfonamide.

23. A process according to claim 1, wherein the base comprises at least one of lithium hydroxide, sodium hydroxide, potassium hydroxide, rubidium hydroxide, cesium hydroxide or barium hydroxide.

24. A process according to claim 1, wherein the first solvent comprises at least one of di(ethylene glycol) ether or 1,3-dimethylimidazolinium dimethyl phosphate.

25. A process according to claim 10, wherein the base is N-methylmorpholine.

* * * * *